(12) United States Patent
Aboul-Hosn et al.

(10) Patent No.: US 8,029,491 B2
(45) Date of Patent: Oct. 4, 2011

(54) METHOD AND APPARATUS FOR PREVENTING AIR EMBOLISMS

(75) Inventors: Walid N Aboul-Hosn, Fair Oaks, CA (US); William R Kanz, Sacramento, CA (US); Jonathan Spangler, Sacramento, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 283 days.

(21) Appl. No.: 10/677,468

(22) Filed: Oct. 2, 2003

(65) Prior Publication Data

US 2004/0073167 A1 Apr. 15, 2004

Related U.S. Application Data

(62) Division of application No. 09/786,703, filed as application No. PCT/US99/22572 on Sep. 30, 1999, now Pat. No. 6,641,558.

(60) Provisional application No. 60/102,561, filed on Sep. 30, 1998.

(51) Int. Cl.
*A61M 31/00* (2006.01)

(52) U.S. Cl. ........ 604/506; 604/507; 604/510; 604/513; 604/35; 604/28

(58) Field of Classification Search .............. 604/4.01, 604/6.11, 28, 35, 506, 507, 510, 513, 532, 604/537, 122, 264, 500, 123, 143, 23, 26, 604/27, 93.01, 149; 623/3.1, 3.26, 3.3, 16; 600/16
See application file for complete search history.

(56) References Cited

U.S. PATENT DOCUMENTS

| | | | | |
|---|---|---|---|---|
| 3,995,617 | A * | 12/1976 | Watkins et al. | 600/16 |
| 4,684,364 | A * | 8/1987 | Sawyer et al. | 604/123 |
| 4,722,725 | A | 2/1988 | Sawyer et al. | |
| 4,955,857 | A * | 9/1990 | Shettigar | 604/6.06 |
| 5,158,553 | A * | 10/1992 | Berry et al. | 604/167.03 |
| 5,441,486 | A * | 8/1995 | Yoon | 604/167.03 |
| 5,755,687 | A | 5/1998 | Donlon | |
| 5,849,005 | A | 12/1998 | Garrison et al. | |
| 6,027,476 | A | 2/2000 | Sterman et al. | |
| 6,106,497 | A | 8/2000 | Wang | |
| 6,858,001 | B1 * | 2/2005 | Aboul-Hosn | 600/16 |

* cited by examiner

*Primary Examiner* — Patricia Bianco
*Assistant Examiner* — Camtu Nguyen
(74) *Attorney, Agent, or Firm* — Alan W. Cannon; Law Office of Alan W. Cannon (57) ABSTRACT

Method and apparatus for preventing air embolisms during surgical procedures which involves providing a fluid source in communication with an aperture extending into an anatomical cavity such that fluid may be delivered into the cavity when a condition of negative pressure exists in the cavity, thereby preventing the introduction of air into the cavity.

13 Claims, 10 Drawing Sheets

METHOD AND APPARATUS FOR PREVENTING AIR EMBOLISMS

CROSS-REFERENCE TO RELATED APPLICATIONS

This application is a divisional of U.S. patent application Ser. No. 09/786,703 filed Jun. 28, 2001, now U.S. Pat. No. 6,641,558 entitled "Method and Apparatus for Preventing Air Embolisms," which is a 35 U.S.C. §371 filing of PCT/US99/22572, filed Sep. 30, 1999, which claims the benefit of U.S. Provisional Application Ser. No. 60/102,561 filed on Sep. 30, 1998, entitled "Embolism Prevention Cannula."

BACKGROUND OF THE INVENTION

I. Field of the Invention

The present invention relates to a safety arrangement for medical procedures. More particularly, the present invention involves a method and apparatus for preventing air embolisms during medical procedures involving the access of anatomical cavities.

II. Brief Description of the Related Art

Introducing instruments into anatomical cavities is commonplace in a wide variety of medical procedures. In cardiac surgery, cannulas are introduced into the various chambers of the heart to re-route blood within and/or outside the heart. Intravascular devices, such as catheters and guidewires, are commonly introduced into the vascular system of a patient in cardiology procedures. Accessing major anatomical cavities, such as the thoracic cavity, may be accomplished through the use of such instruments as trocars. In each instance, the introduction of air into the anatomical cavity being accessed is undesirable in that it can present the possibility of air embolism formation. In the circulatory system, for example, air embolisms pose the danger of a stroke to the patient. One cause for the introduction of air into the cavity being accessed is when the pressure within the cavity is sufficiently lower than outside the cavity. When such a negative pressure differential exists inside the cavity, the resulting suction force can draw air from outside the cavity into the cavity.

The present invention is directed at overcoming the above-identified problem of air being drawn into an anatomical cavity due to a negative pressure differential developing therein.

SUMMARY OF THE INVENTION

One aspect of the present invention involves providing a method of preventing air embolisms. The method comprises the steps of: (a) providing a fluid source in communication with an aperture extending into an anatomical cavity; and (b) delivering fluid from the fluid source into the anatomical cavity when a condition of negative pressure exists in the anatomical cavity.

One embodiment of the method includes the steps of providing a fluid delivery conduit in communication with the aperture of the anatomical cavity, and coupling the fluid source to the fluid delivery conduit to deliver fluid into the anatomical cavity.

One embodiment of the method includes the steps of providing the fluid delivery conduit with a first opening and a second opening, and providing a sealing member across the first opening of the fluid delivery conduit.

One embodiment of the method includes the steps of providing an aperture in the sealing member, introducing an instrument through the aperture in the sealing member, and extending the instrument into the anatomical cavity.

One embodiment of the method includes the steps of providing a second sealing member across the second opening of the fluid delivery conduit, providing an aperture in the second sealing member, passing the instrument through the aperture in the sealing member, and extending the instrument into the anatomical cavity.

One embodiment of the method includes the step of positioning the fluid delivery conduit such that the fluid delivery conduit extends through the aperture into the anatomical cavity.

One embodiment of the method includes the step of positioning the fluid delivery conduit such that the fluid delivery conduit does not extend through the aperture into the anatomical cavity.

One embodiment of the method includes the step of controlling the delivery of fluid from the fluid source based on a parameter indicative of a negative pressure within the anatomical cavity.

In one embodiment of the method, the parameter may comprise one of pressure within the anatomical cavity, pressure outside the anatomical cavity, flow rate of fluid being delivered into the anatomical cavity, oxygen content of fluid within the anatomical cavity, and oxygen content of fluid being removed from the anatomical cavity.

One embodiment of the method includes the step of controlling the delivery of fluid from the fluid source based on a parameter indicative of a negative pressure within the anatomical cavity. Also provided is the step of selecting the parameter from at least one of pressure within the anatomical cavity, pressure within the fluid delivery conduit, flow rate of fluid through the fluid delivery conduit, oxygen content of fluid within the anatomical cavity, and oxygen content of fluid being removed from the anatomical cavity.

In another aspect of the present invention, an apparatus for preventing air embolisms is provided. The apparatus comprises a fluid source in communication with an aperture extending into an anatomical cavity such that fluid may be delivered into the anatomical cavity when a condition of negative pressure exists in the anatomical cavity.

One embodiment of the apparatus includes a fluid delivery conduit in communication with the aperture. The fluid delivery conduit is coupled to the fluid source to deliver fluid into the anatomical cavity.

In one embodiment of the apparatus, the fluid delivery conduit includes a first opening and a second opening, and a sealing member is disposed across the first opening of the fluid delivery conduit.

In one embodiment of the apparatus, the sealing member includes an aperture for receiving an instrument therethrough.

One embodiment of the apparatus includes a second sealing member disposed across the second opening of the fluid delivery conduit. The second sealing member includes an aperture for receiving the instrument therethrough.

In one embodiment of the apparatus, the fluid delivery conduit is positioned to extend into the anatomical cavity.

In one embodiment of the apparatus, the fluid delivery conduit is positioned such that the fluid delivery conduit does not extend into the anatomical cavity.

One embodiment of the apparatus includes a controller for controlling the delivery of fluid from the fluid source based on a parameter indicative of a negative pressure within the anatomical cavity.

In one embodiment of the apparatus, the parameter comprises one of pressure within the anatomical cavity, pressure outside the anatomical cavity, flow rate of fluid being delivered into the anatomical cavity, oxygen content of fluid within the anatomical cavity, and oxygen content of fluid being removed from the anatomical cavity.

One embodiment of the apparatus includes a controller for controlling the delivery of fluid from the fluid source based on a parameter indicative of a negative pressure within the anatomical cavity.

In one embodiment of the apparatus, the controller includes a sensor for sensing at least one of the parameters.

In one embodiment of the apparatus, the parameter comprises at least one of pressure within the anatomical cavity, pressure within the fluid delivery conduit, flow rate of fluid through the fluid delivery conduit, oxygen content of fluid within the anatomical cavity, and oxygen content of fluid being removed from the anatomical cavity.

In a still further aspect of the present invention, a system is provided for preventing air embolisms during medical procedures involving introducing an instrument into an anatomical cavity. The system comprises a fluid delivery conduit in communication with an aperture extending into the anatomical cavity. A fluid source is coupled to the fluid delivery device for delivering fluid into the anatomical cavity when a condition of negative pressure exists within the anatomical cavity.

One embodiment of the system includes a controller for controlling the pressure within the anatomical cavity.

In one embodiment of the system, the controller includes a pump for selectively delivering fluid into the anatomical cavity in response to the condition of negative pressure within the anatomical cavity.

In one embodiment of the system, the pump controls the flow of fluid from the fluid source.

In one embodiment of the system, the pump controls the flow of fluid through a cannula extending into the anatomical cavity.

One embodiment of the system includes a sensor for sensing a parameter indicative of a negative pressure within the anatomical cavity.

In one embodiment of the system, the parameter comprises at least one of pressure within the anatomical cavity, pressure within the fluid delivery conduit, flow rate of fluid through the fluid delivery conduit, oxygen content of fluid within the anatomical cavity, and oxygen content of fluid being removed from the anatomical cavity.

In one embodiment of the system, the sensor comprises at least one of a pressure sensor, a flow sensor, an oxygen sensor, a motor speed sensor, a pump output sensor, and a strain gauge.

Another aspect of the present invention involves providing a method of preventing air embolisms comprising the step of reducing or eliminating a condition of negative pressure within an anatomical cavity such that air will not be drawn through an aperture extending into the anatomical cavity.

One embodiment of the method includes the step of delivering fluid into the anatomical cavity when the condition of negative pressure occurs within the anatomical cavity.

One embodiment of the method includes the step of the step of delivering the fluid through the use of a fluid source in communication with the anatomical cavity.

In one embodiment of the method, the fluid source delivers the fluid into the anatomical cavity through a fluid delivery conduit extending through the aperture into the anatomical cavity.

One embodiment of the method includes the step of controlling the withdrawal of fluid from the anatomical cavity to reduce or eliminate the negative pressure.

One embodiment of the method includes the step of stopping the withdrawal of fluid from the anatomical cavity to reduce or eliminate the negative pressure.

One embodiment of the method includes the step of varying withdrawal of fluid from the anatomical cavity to reduce or eliminate the negative pressure.

One embodiment of the method includes the step of controlling the reduction or elimination of the negative pressure based on a parameter indicative of a negative pressure within the anatomical cavity.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

A method and apparatus is provided for preventing air embolisms during medical procedures involving the access of anatomical cavities. As will be explained hereinafter, the present invention involves providing a fluid source in communication with an aperture or opening extending into an anatomical cavity such that fluid will be delivered into the cavity when a condition of negative pressure develops therein. In this fashion, fluid from the fluid source will be delivered into the cavity, as opposed to air or other unwanted substances that may otherwise be drawn into the cavity due to the suction force inside the cavity. The fluid that supplants the possible introduction of air may be any of a variety of suitable fluids (liquids and/or gases), including but not limited to saline, blood, and carbon dioxide. Supplanting air with such fluids prevents the formation of air embolisms within the anatomical cavity being accessed, thereby reducing the risk of complications related to air embolisms.

Figure 1:
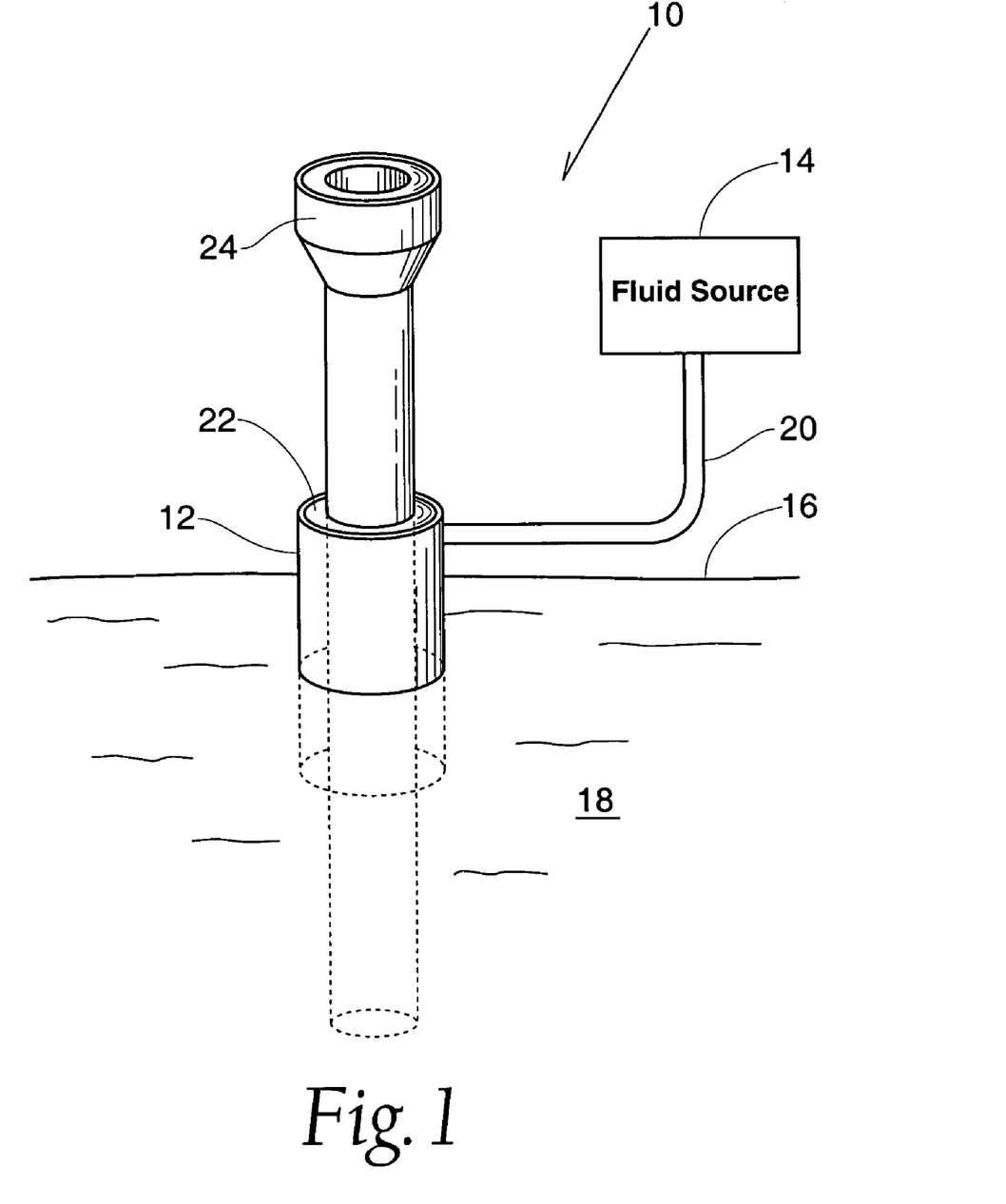
FIG. 1 is a perspective view of an air embolism prevention system according to an exemplary embodiment of the present invention.
Figure 2:
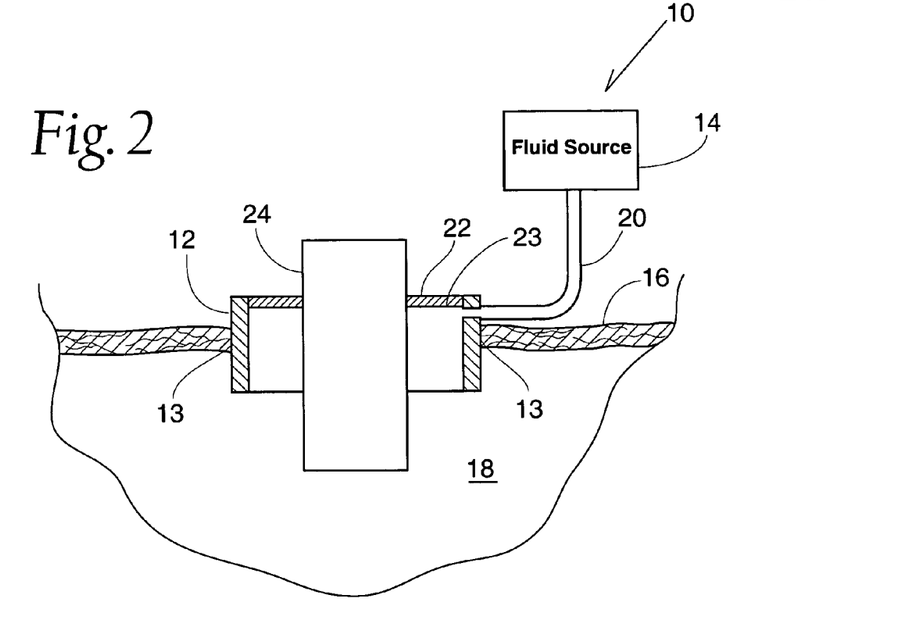
FIG. 2 is a partial cross-sectional view of an air embolism prevention system of the type shown in FIG. 1.

FIGS. 1 and 2 collectively illustrate an air embolism prevention system 10 according to an exemplary embodiment of the present invention. The system 10 includes a fluid delivery conduit 12 and a fluid source 14. The fluid delivery conduit 12 extends through an aperture 13 formed in anatomical tissue 16 into an anatomical cavity 18. The aperture 13 comprises an opening formed in the tissue 16 to provide access to the underlying anatomical cavity 18. After formation, the aperture 13 may be closed or secured about the fluid delivery conduit 12 using any number of known leakage-prevention techniques, including but not limited to the use of so-called "purse string" sutures. As is known in the art, such purse-string sutures are disposed in the tissue 16 surrounding the aperture 13 and may be selectively tightened in an effort to seal the aperture 13 about the particular device extending though the aperture 13 (in this case, the fluid delivery conduit 12).

The fluid source 14 is coupled to the fluid delivery conduit 12 via a supply conduit 20. In the embodiment shown, the fluid delivery conduit 12 is provided with a flexible sealing member 22 disposed across opening 23 capable of allowing an instrument 24 to be passed through the fluid delivery conduit 12 into the anatomical cavity 18. The sealing member 22 may be comprised of any known valve-type material, such as those employed in known hemostasis valves. The sealing member 22 prohibits air or other unwanted substances from entering the cavity 18 before, during, and after the instrument 24 is introduced into the cavity 18. The fluid source 14 may comprise any number of suitable fluid supply systems, including but not limited to a saline-filled intravenous (IV) drip bag, a pumping system, or a gas delivery system for transporting gas such as carbon-dioxide to the fluid delivery conduit 12.

The fluid delivery conduit 12 may be constructed from any material suitable for introduction into the human body, including but not limited to plastic or stainless steel. The fluid delivery conduit 12 may take any number of geometric configurations, including but not limited to cylindrical. Various structures may be provided on the fluid delivery conduit 12 to provide a guiding function for the instrument 24. The fluid delivery conduit 12 may also include a variety of structures or elements to facilitate introducing, positioning, and/or securing the fluid delivery conduit 12 with respect to the aperture 13 and/or anatomical cavity 18.

The air embolism prevention system 10 of the present invention is designed to deliver fluid from the fluid source 14 through the fluid delivery conduit 12 and into the anatomical cavity 18 when a condition of negative pressure develops therein. A condition of negative pressure may result in anatomical cavity 18 if, for example, a pumping arrangement is used to withdraw fluid from within the cavity 18. Such a pumping arrangement may extend into the cavity 18 through the fluid delivery conduit 18, or through a separate aperture. In either case, the resulting suction force that develops within the anatomical cavity 18 (in the absence of fluid delivery according to the present invention) may be sufficient to draw air or other unwanted substances through the junction between the fluid delivery conduit 12 and the aperture 13 formed in the tissue 16. In other words, the suction force within the cavity 18 may be strong enough to overcome the "anti-leakage" capability of the purse-string suture that closes the aperture 13 about the fluid delivery conduit 12, thereby allowing air or other substances to be drawn into the cavity 18.

In one embodiment, the present invention solves this potential problem by delivering fluid from the fluid source 14 into the cavity 18 when negative pressure develops therein. In this fashion, the fluid being delivered into the anatomical cavity 18 will take the place of air or other substances that would otherwise be drawn into the cavity 18. Fluid delivery from the source 14 may be driven by the pressure differential itself, i.e. by maintaining an ample supply of fluid (gas and/or liquid) in the fluid source 14 at a pressure equal to or greater than the ambient pressure outside the cavity 18. In this manner, the fluid may flow through the fluid delivery conduit 12 and into the cavity 18 if the pressure within the cavity 18 drops below the pressure outside the cavity 18.

As will be explained below, feedback and control features may also be provided to control or drive the delivery of fluid from the fluid source 14 in an active fashion, such as through the use of a pump or the like. The present invention may also reduce or eliminate the formation of negative pressure within the anatomical cavity 18 by controlling the introduction of other fluids into the cavity 18, such as fluid being delivered into or out of the cavity 18 using a cannulation system. That is to say, the delivery or withdrawal of fluid into or from the anatomical cavity 18 by such a cannulation system may be varied (increased or decreased) or stopped altogether to reduce if not eliminate the negative pressure being developed within the cavity 18.

The air embolism prevention system 10 of the present invention finds use in a wide variety of medical applications. The anatomical cavity 18 shown generally in FIGS. 1 and 2 may comprise any number of anatomical cavities within a patient, including but not limited to the thoracic cavity, blood vessels, heart chambers, and body organs such as the stomach, intestines, etc. In similar fashion, instrument 24 may comprise any of a variety of other instruments capable of being introduced into an anatomical cavity, including but not limited to trocars, cannulas, catheters, guidewires, introducers, and surgical instruments. In so doing, the air embolism prevention system 10 of the present invention provides the ability to prevent the unwanted introduction of air or other substances during virtually any medical procedure involving the introduction of an instrument into an anatomical cavity.

Figure 3:
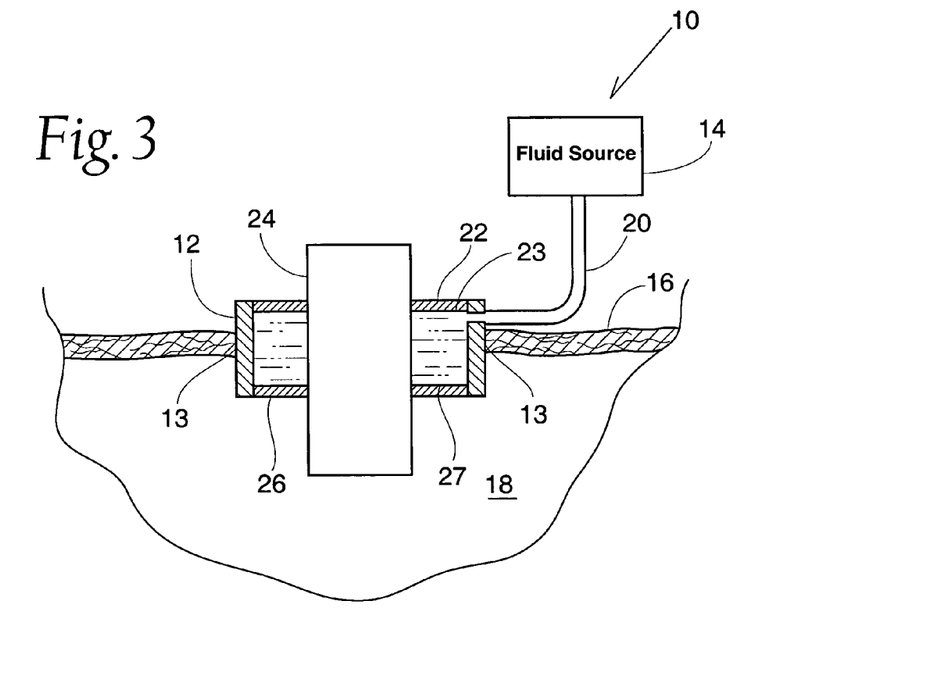
FIG. 3 is a partial cross-sectional view of an air embolism prevention system according to an exemplary embodiment of the present invention.

FIG. 3 illustrates another exemplary embodiment of the air embolism prevention system 10 according to the present invention. In this embodiment, the air embolism prevention system 10 includes a second sealing member 26 disposed over a second opening 27 proximate to the distal portion of the fluid delivery conduit 12. The sealing member 26 is preferably constructed of a flexible material of the type used for the sealing member 22, and includes a distendable aperture forming a fluid-seal around the instrument 24. In this fashion, the sealing member 26 operates to maintain a supply of fluid within the fluid delivery conduit 12 without immediate delivery into the anatomical cavity 18. The characteristics of the sealing member 26 are selected such that it will distend and allow fluid from within the fluid delivery conduit 12 to flow into the anatomical cavity 18 when a predetermined pressure differential is developed between the interior of the fluid delivery conduit 12 and the cavity 18. That is to say, the sealing member 26 is selected such that fluid from within the fluid delivery member 12 will be drawn into the cavity 18 before air or other unwanted substances can be drawn into the cavity 18 past the purse-string suture around the fluid delivery conduit 12.

Figure 4:
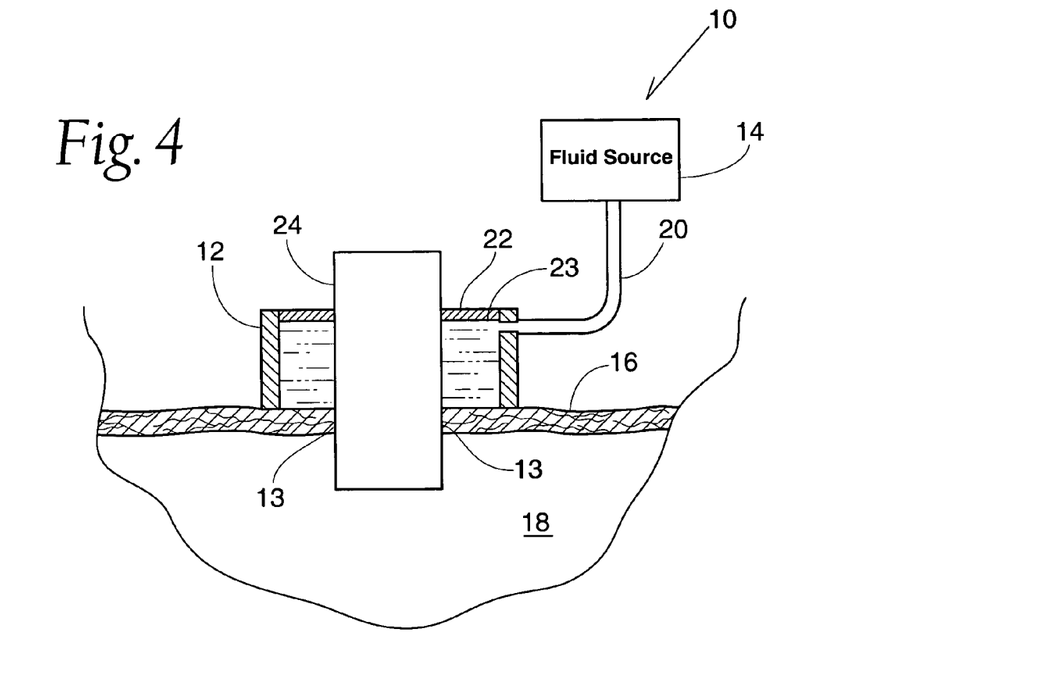
FIG. 4 is a partial cross-sectional view of an air embolism prevention system according to an exemplary embodiment of the present invention.
Figure 5:
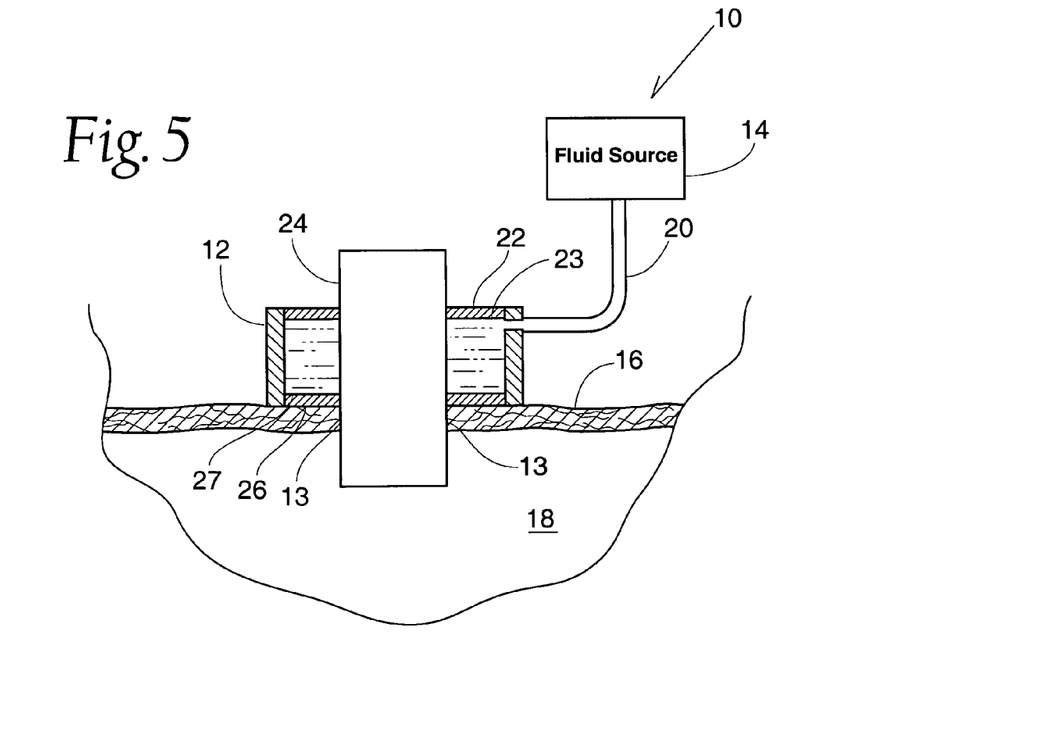
FIG. 5 is a partial cross-sectional view of an air embolism prevention system according to an exemplary embodiment of the present invention.

FIGS. 4 and 5 illustrate still further embodiments of the air embolism prevention system 10 according to the present invention. In each case, the fluid delivery conduit 12 is positioned over, and in communication with, the aperture 13 formed in the tissue 16.

In FIG. 4, the tissue 16 itself operates to maintain a supply of fluid within the fluid delivery conduit 12 without immediate delivery into the anatomical cavity 18. In FIG. 5, the second sealing element 26 serves this function. The fluid delivery conduit 12 in both embodiments is maintained against the tissue 16 with sufficient force or adhesion such that a negative pressure differential within the cavity 18 will draw fluid from within the fluid deliver conduit 12 into the anatomical cavity 18. Loosening or eliminating the purse-string suture around the fluid delivery conduit 12 may facilitate the flow of fluid from the fluid delivery conduit 12 into the cavity 18.

The sealing element 26 in FIG. 5 is selected such that it will distend and allow fluid from within the fluid delivery conduit 12 to flow into the anatomical cavity 18 instead of air or other unwanted substances that might otherwise be drawn past the junction between the fluid delivery conduit 12 and the tissue 16 and onward into the cavity 18 due to a negative pressure differential therein.

The air embolism prevention systems 10 of FIGS. 4 and 5 are also distinguishable in that they can be positioned after the instrument 24 has been introduced through the tissue 16 and into the cavity 18. This provides the ability to retrofit an existing cavity access site to prevent air embolisms.

As noted above, the method and apparatus of the present invention can be used in virtually any medical procedure involving accessing an anatomical cavity with an instrument. Below are illustrative examples of several such applications.

Figure 6:
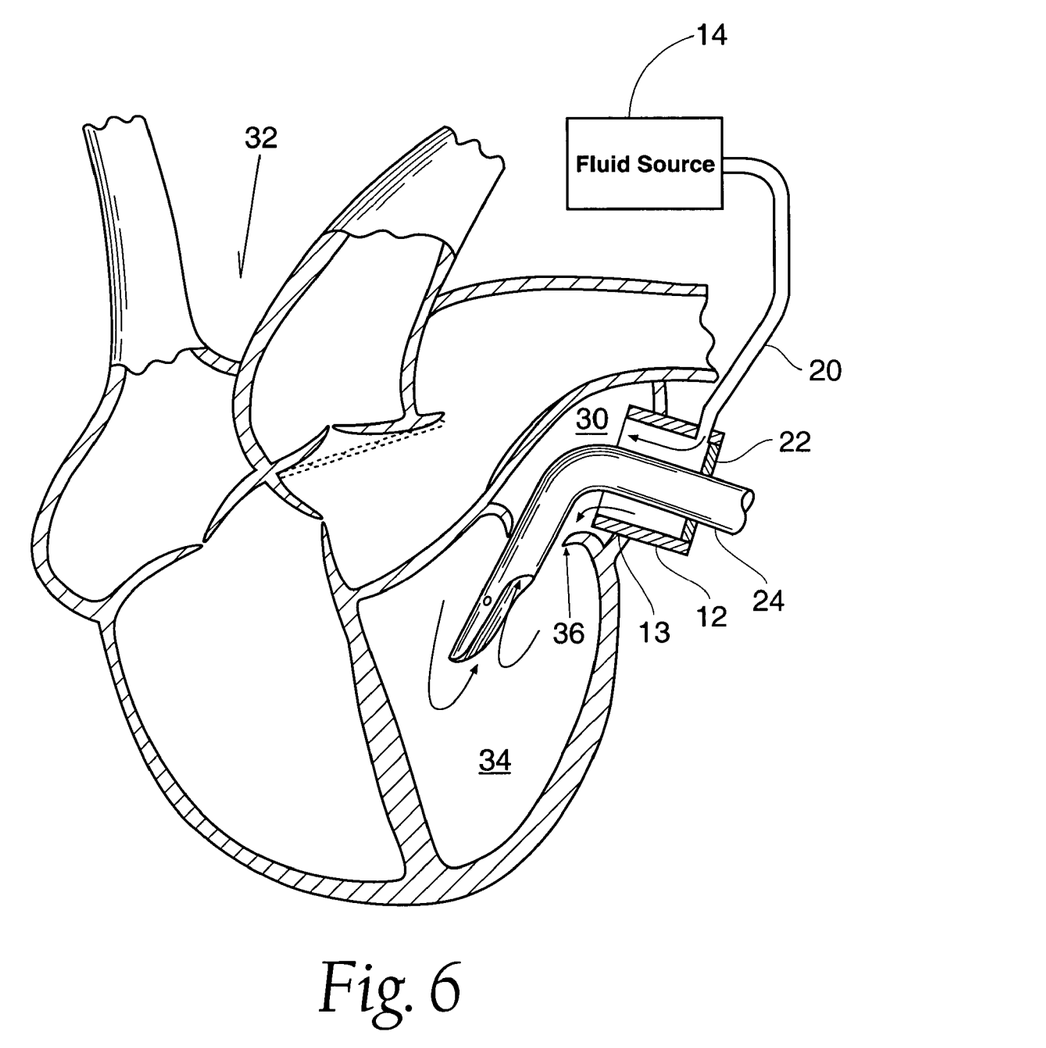
FIG. 6 is a partial sectional view of an air embolism prevention system according to the present invention employed as part of a left-ventricular assist cannulation procedure.

FIG. 6 illustrates an air embolism prevention system according to the present invention employed as part of a left-ventricular assist cannulation procedure during beating-heart cardiac surgery. In this embodiment, the fluid delivery conduit 12 extends into the left atrium 30 of a heart 32, and the instrument 24 comprises a cannula member configured to extend into the left ventricle 34. The cannula 24 is coupled to a blood pump (not shown), which exerts a suction force within the left ventricle 34 for the removal of blood therefrom. Removing blood in this fashion serves to "unload" the left ventricle 34. During beating-heart cardiac surgery, including but not limited to coronary artery bypass graft (CABG) procedures, such "unloading" is helpful in that it serves to stabilize the heart tissue to reduce the challenge of operating on a beating heart.

This withdrawal of blood also creates a negative pressure differential inside the left ventricle 34. Depending upon the rate at which blood is removed, this negative pressure differential may become strong enough to draw blood from the left atrium 30 through the mitral valve 36 and into the left ventricle 34. If this occurs, a negative pressure differential may develop within the left atrium 30. Without the air embolism prevention system of the present invention, the negative pressure within the left atrium 30 could potentially develop to a strength sufficient to draw air past the purse-string suture used to close off the aperture 13 formed in the wall of the left atrium 30.

The air embolism prevention system of the present invention prevents this problem by providing the fluid source 14 in communication with the left atrium 30. More specifically, fluid will be drawn or otherwise delivered into the left atrium 30 so as to reduce, if not eliminate, the pressure differential that might otherwise develop between the blood within the left atrium 30 and the air outside the heart 32. In so doing, any negative pressure that does develop within the left atrium 30 will be of insufficient strength to draw air past the purse-string suture around the fluid delivery conduit 12, thereby preventing the risk of air embolisms.

Figure 7:
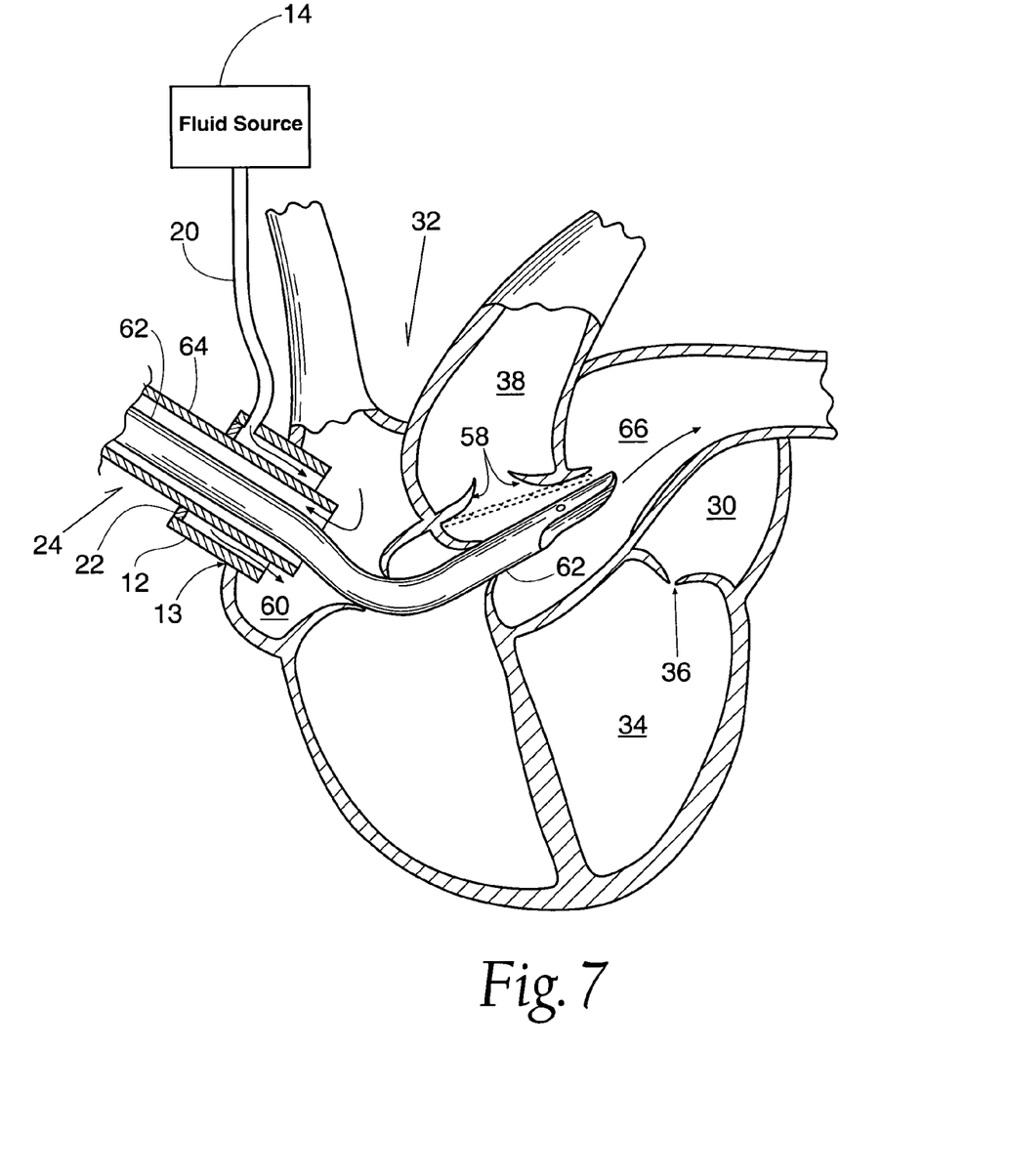
FIG. 7 is a partial sectional view of an air embolism prevention system according to the present invention employed as part of a right-ventricular assist cannulation procedure.

FIG. 7 illustrates an air embolism prevention system according to the present invention employed as part of a right-ventricular assist cannulation procedure for beating-heart cardiac surgery. The fluid deliver conduit 12 extends into the right atrium 60. In this embodiment, the instrument 24 comprises a coaxial cannulation assembly having an inner cannula 62 disposed in a generally coaxial fashion within an outer cannula 64. The outer cannula 64 extends through the sealing member 22 of the fluid delivery conduit 12 into the right atrium 60. The inner cannula 62 is configured to extend into the pulmonary artery 66. To provide right-ventricular assist, the outer cannula 64 is used to withdraw fluid from the right atrium 60, while the inner cannula 62 is used to re-route this blood into the pulmonary artery 66.

Figure 8:
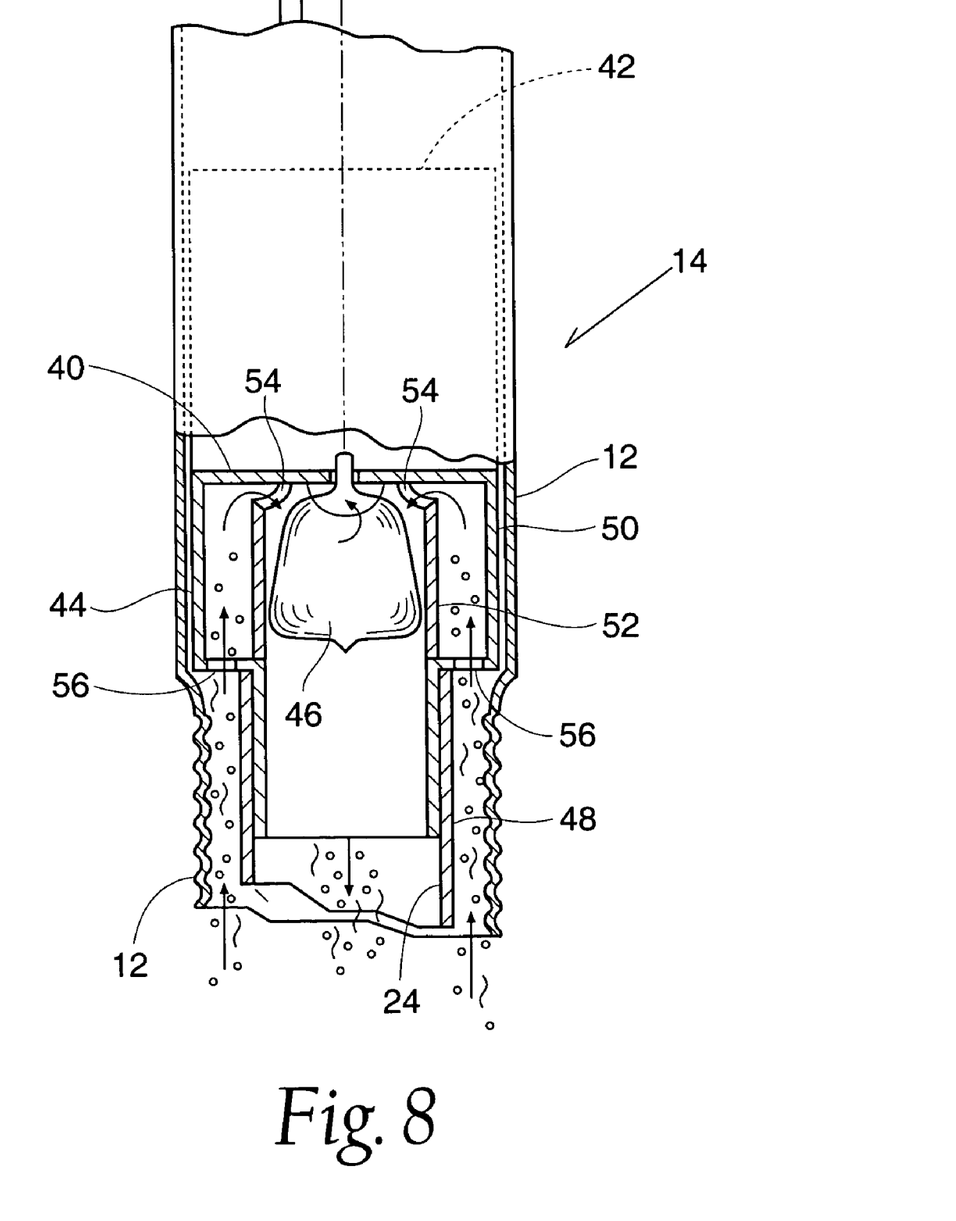
FIG. 8 is a partial sectional view of a reverse flow blood pump for use as part of the coaxial cannulation system shown in FIG. 7 which extends through an air embolism prevention system according to the present invention.

To accomplish this right-ventricular assist function, the inner and outer cannulas 62, 64 may be coupled, by way of example only, to a reverse flow pumping system of the type shown in FIG. 8, which is described in detail in co-pending and commonly-assigned U.S. patent application Ser. No. 08/891,456, the contents of which are hereby expressly incorporated by reference. The reverse flow pumping system includes a pump 40 coupled to a motor 42. The pump 40 includes a cylindrically shaped housing body 44 and a rotor 46. The housing body 44 is disposed generally within or coupled to the outer cannula 64. The housing body 44 includes an extending neck portion 48 for connection to the inner cannula 62, and a base portion 50 having an inner tubular element 52 co-aligned with the neck portion 48. A plurality of flow apertures 54 and 56 are provided such that, under the direction of the rotor 46, fluid will be drawn through the outer cannula 64 into the base portion 50 and redirected in a radially inward direction through the flow apertures 54 and then in a reverse direction out the inner cannula 62.

During the right-ventricular assist function carried out by the aforementioned coaxial cannulation system, the outflow of blood from the right atrium 60 through the outer cannula 64 may create a negative pressure within the right atrium 60. Without the fluid delivery feature of the present invention, this negative pressure may become sufficiently strong so as to overcome the fluid-sealing properties of the purse-string suture about the fluid delivery device 12 and/or the sealing member 22 about the outer cannula 64, allowing air or other unwanted substances to be drawn into the right atrium 60.

The system of the present invention prevents this by supplying fluid through the fluid delivery conduit 12 into the right atrium 60. This serves to reduce, if not eliminate, the pressure differential that might otherwise develop between the blood within the right atrium 60 and the air outside the heart 32. Any negative pressure that does develop within the left atrium 60 will be of insufficient strength to draw air past the purse-string suture around the fluid delivery conduit 12 or past the sealing member 22. As will be appreciated by those skilled in the art, this aids in the prevention of air embolisms.

Figure 9:
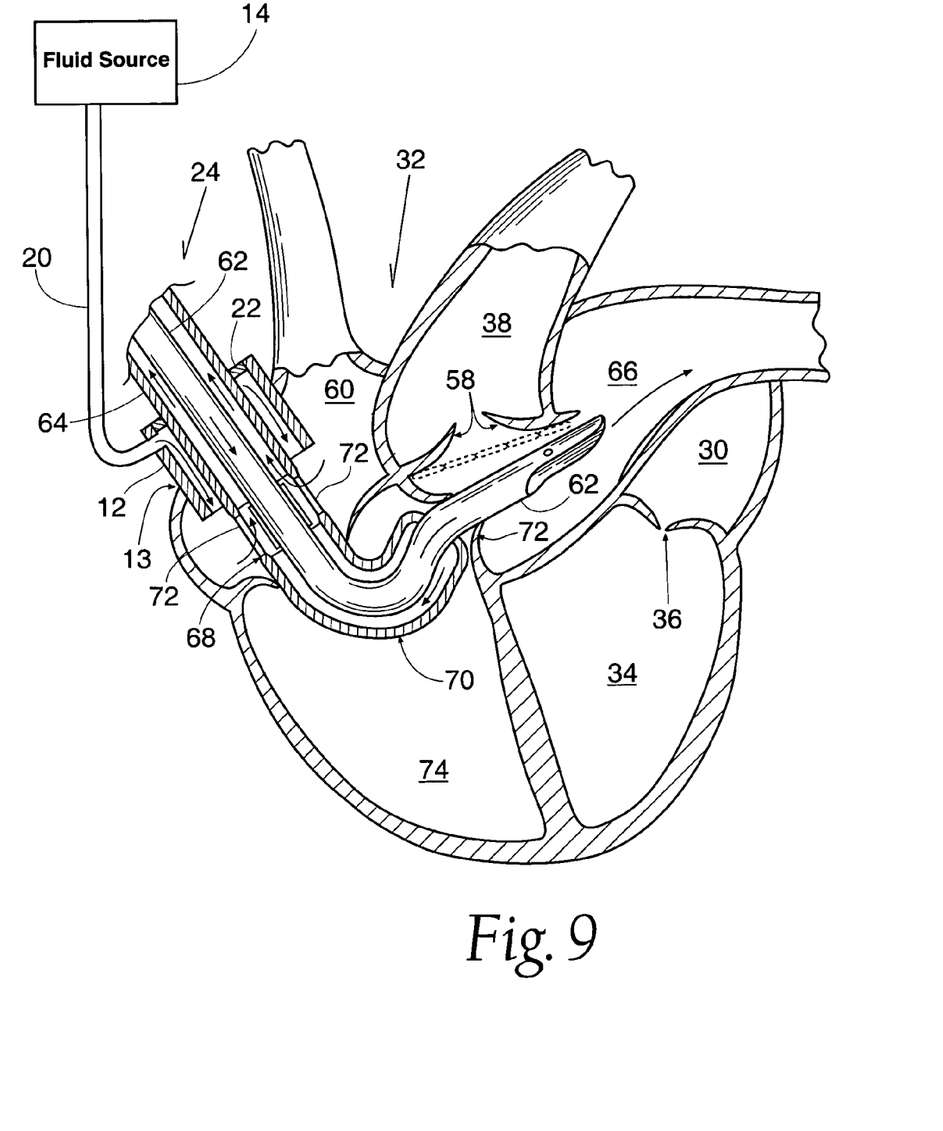
FIG. 9 is a partial sectional view of an air embolism prevention system according to the present invention employed as part of a right-ventricular assist cannulation procedure.

FIG. 9 illustrates an air embolism prevention system according to the present invention employed as part of another right-ventricular assist cannulation procedure for beating-heart cardiac surgery. In this embodiment, the instrument 24 comprises a coaxial cannulation system of the type described above, except that the outer cannula 64 includes a fluid inlet section 68 and a "J-tip" section 70. The fluid inlet section 68 includes a plurality of flow apertures 72 allowing blood within the right atrium 60 to be withdrawn through the outer cannula 64. The "J-tip" section 70 extends into the right ventricle 74 or pulmonary artery 66 and serves to guide the inner cannula 62 through the pulmonary valve 76 into position within the pulmonary artery 66.

As with the embodiment shown in FIG. 7, the outflow of blood through the outer cannula 64 may create a negative pressure within the right atrium 60 which, in the absence of the fluid delivery system of the present invention, may develop to the point that it overcomes the sealing ability of the purse-string suture about the fluid delivery device 12 and/or the sealing member 22 about the outer cannula 64, allowing air or other unwanted substances to be drawn into the right atrium 60. According to the present invention, this potential problem is avoided by supplying fluid through the fluid delivery conduit 12 into the right atrium 60 to reduce, if not eliminate, the pressure differential that might otherwise develop between the blood within the right atrium 60 and the air outside the heart 32.

Figure 10:
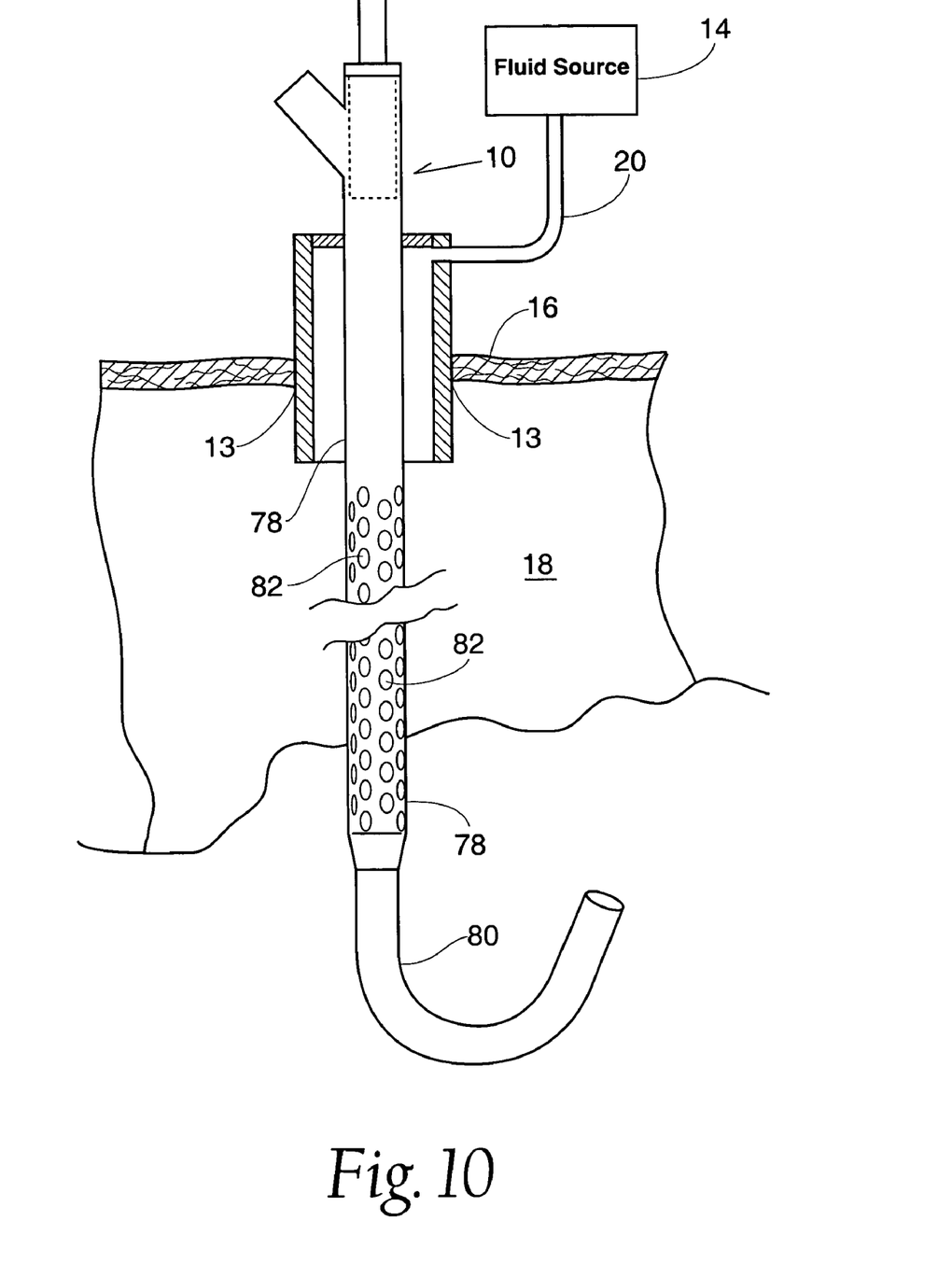
FIG. 10 is a partial sectional view of an air embolism prevention system according to the present invention employed with an intravascular cannulation system for use in a right-ventricular assist procedure.

FIG. 10 illustrates an air embolism prevention system according to the present invention employed with an intravascular cannulation system for use in a right-ventricular assist procedure. In this embodiment, the fluid delivery conduit 12 extends through the tissue 16 of a blood vessel into the vascular lumen 18 disposed therein. The instrument 24 is shown, by way of example, as an intravascular cannulation system comprising an outer cannula 78 and an inner cannula 80 disposed in a generally coaxial fashion within the outer cannula 78.

Figure 11:
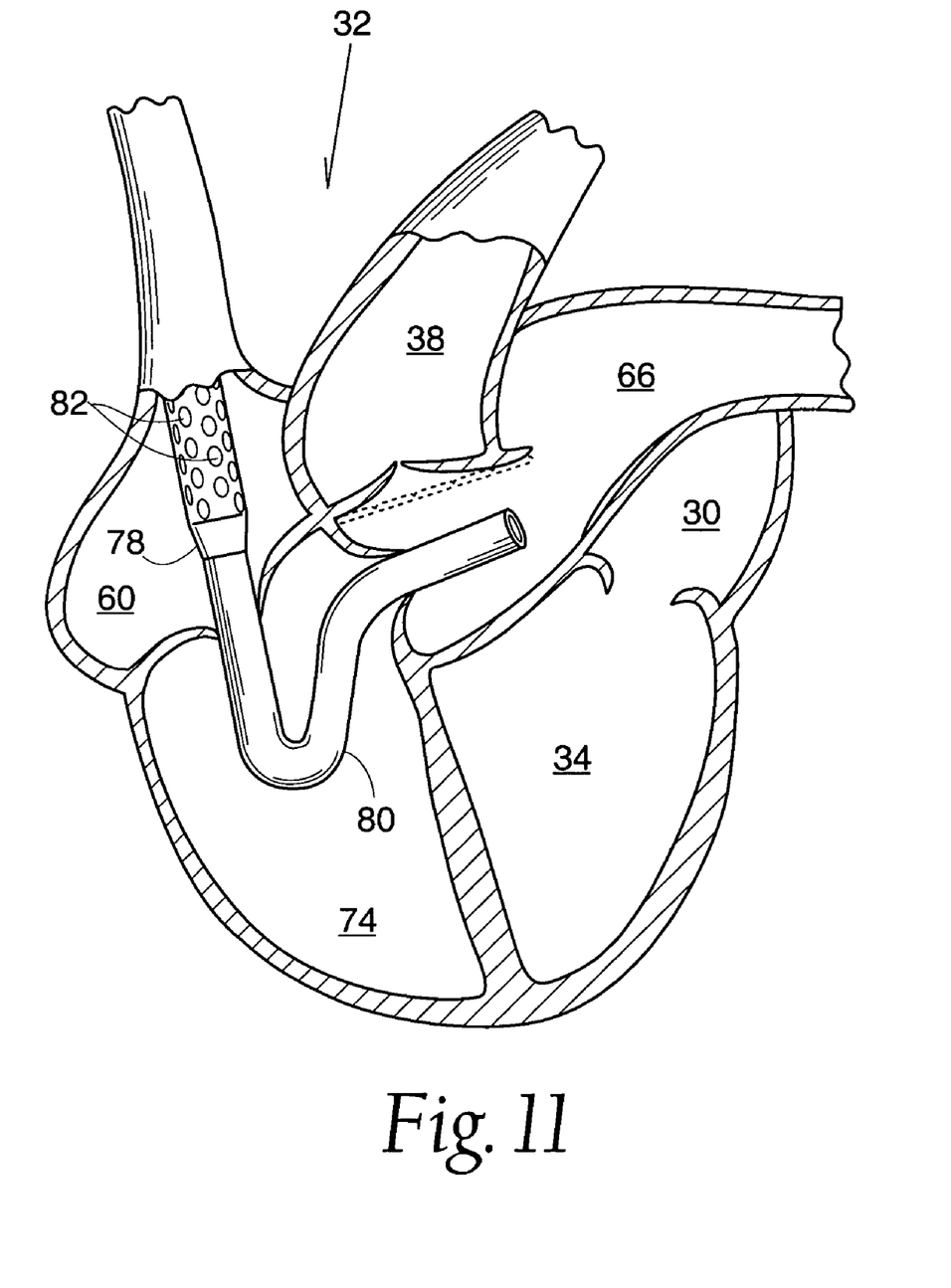
FIG. 11 is a partial sectional view of the intravascular cannulation system shown in FIG. 10 during a right-ventricular assist procedure.

To provide right-ventricular assist, the instrument 24 may be introduced into any vessel within the vascular system that allows the outer and inner cannulas 78, 80 to be positioned within the heart 32 as shown in FIG. 11. The jugular vein is an example of one such vessel. The outer cannula 78 is positioned within the right atrium 60 such that flow apertures 82 formed in the outer cannula 78 may be used to withdraw blood from the right atrium 60, and the inner cannula 80 positioned within the pulmonary artery 66.

Any of a variety of pumping systems (not shown) may be employed with the outer and inner cannulas 78, 80 to provide the requisite fluid flow into and out of the heart 32. As shown in FIG. 10, the fluid apertures 82 may extend along a majority of the length of the outer cannula 78. If the fluid apertures 82 are disposed in close proximity to the point of entry into the tissue 16, a negative pressure may develop in that region during the withdrawal of blood through the outer cannula 78. Without the air embolism prevention system of the present invention, it may be possible for this negative pressure to build to the point that it overcomes the sealing capability of the purse-string suture, thereby allowing air or other unwanted substances to enter the vessel 18. Once again, the present invention reduces, if not eliminates, this risk by delivering fluid from the fluid source 14 into the cavity 14 through the fluid delivery conduit 12.

Figure 12:
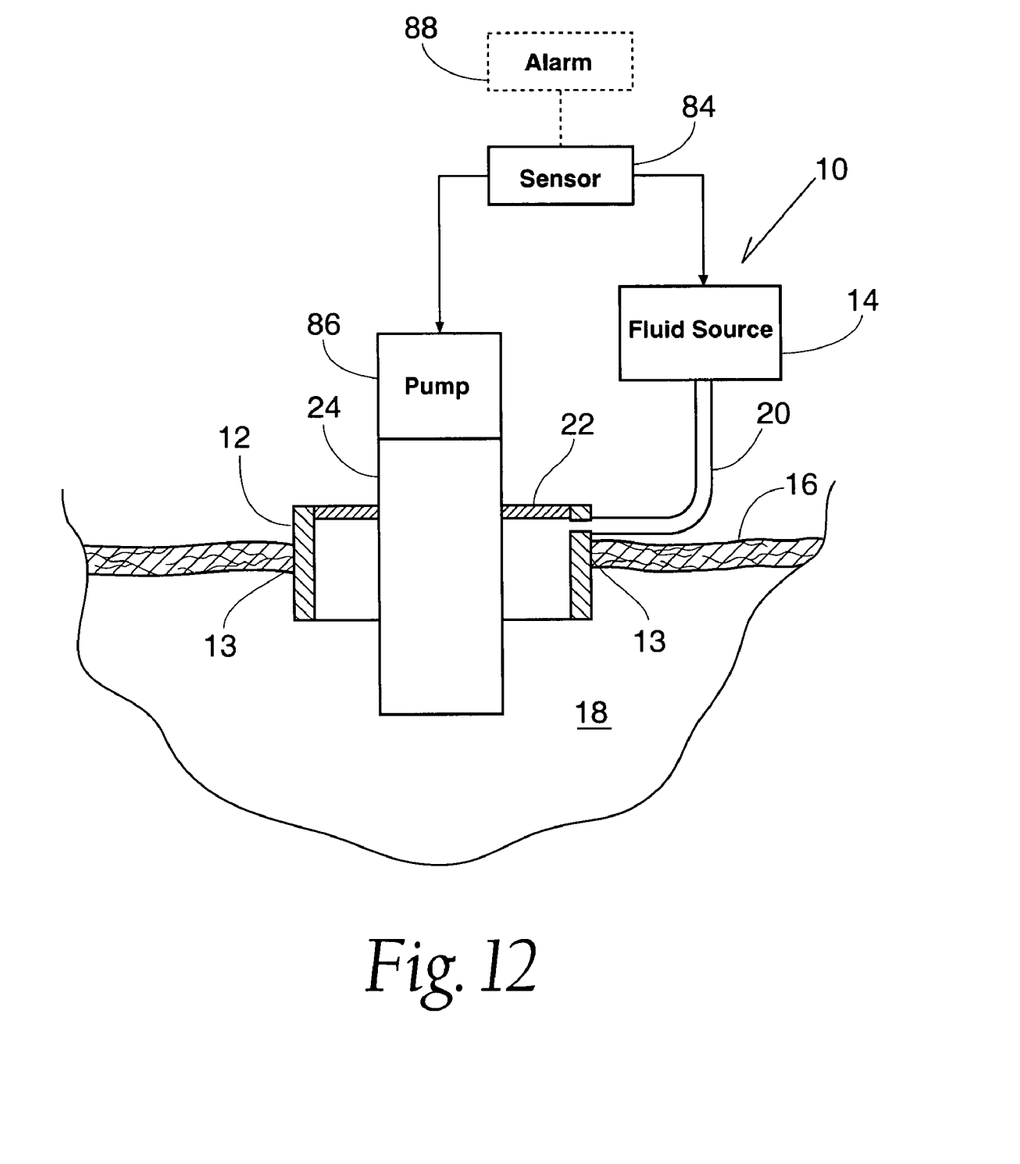
FIG. 12 is a partial sectional view of an air embolism prevention system incorporating various feedback and/or control features according to the present invention.

The air embolism prevention system of the present invention may also incorporate various control and/or feedback features, including but not limited to those set forth by way of example in FIG. 12. The air embolism prevention system 10 may include a sensor 84 for measuring or detecting one of a variety of parameters indicative of a threat or risk of having air or other unwanted substances being drawn into the anatomical cavity 18. Depending upon the parameter which is measured or detected (examples of which will be set forth below), the sensor 84 may be used to control such things as the delivery of fluid from the fluid source 14, the operation of a motor 86 coupled to a cannula 24 for withdrawing fluid from the anatomical cavity 18 (such as in left or right ventricular assist cannulation procedures), as well as an optional alarm 88 for alerting medical personnel that a risk of air introduction exists.

Parameters that may be indicative of a threat or risk of having air or other unwanted substances being drawn into the anatomical cavity 18 may include, but are not necessarily limited to, the pressure within the anatomical cavity 18, the pressure within the fluid delivery conduit 12, supply conduit 20 and/or fluid source 14, the pressure outside the anatomical cavity 18, the flow rate of fluid from the fluid source 14, the flow rate of fluid through the supply conduit 20 and/or fluid delivery conduit 12, the flow rate of fluid being delivered into the anatomical cavity 18 through the cannula 24, the speed and/or flow rate of the pump 86, the oxygen content of the fluid within the anatomical cavity 18, the oxygen content of the fluid being withdrawn from the anatomical cavity 18 via the outflow cannula 24, and the tension or flexion of the sealing member 22.

Sensor 84 may comprise any known device or technique for measuring the above-identified parameters, including but not limited to pressure sensors, flow sensors, oxygen sensors, motor speed sensors, pump output sensors, and strain gauges.

Using any of the foregoing exemplary feedback arrangements, the air embolism prevention system 10 may be controlled to ensure that air or other unwanted substances are not drawn or introduced into the anatomical cavity 18 being accessed. This may be accomplished, by way of example, by stopping the removal of fluid from the anatomical cavity to reduce or eliminate the negative pressure therein, and/or increasing the inflow of fluid through the fluid delivery conduit 12 to reduce or eliminate the negative pressure within the anatomical cavity 18.

A method and apparatus for preventing air embolisms has been described in detail above. The foregoing embodiments are provided by way of example only in an effort to demonstrate the usefulness of the present invention in any medical procedure involving the access of an anatomical cavity. The present invention advantageously provides a fluid source in communication with an aperture extending into an anatomical cavity such that fluid will be delivered into the cavity when a condition of negative pressure develops therein. In this fashion, fluid will be delivered into the cavity, instead of air or other unwanted substances that may otherwise be drawn into the cavity. Supplanting air with such fluids prevents the formation of air embolisms within the anatomical cavity being accessed, thereby reducing the risk of complications related to air embolisms.

While the invention has been described in detail with reference to the preferred embodiments thereof, it will be apparent to one skilled in the art that various changes and modifications can be made and equivalents employed, without departing from the present invention.

What is claimed is:

1. A method of providing left side cardiac support comprising:
   providing a fluid source;
   introducing a fluid delivery conduit into the left atrium, the fluid delivery conduit being in communication with the fluid source via a supply conduit interconnecting the fluid delivery conduit and the fluid source, the fluid delivery conduit further including an opening and a hemostatic seal sealing the opening;
   introducing an intake cannula through the hemostatic seal and opening of the fluid delivery conduit and into the left ventricle, the intake cannula being coupled to a blood pump;

operating the blood pump to intake blood from the left ventricle through the intake cannula, and delivering fluid from the fluid source through the fluid delivery conduit into the left atrium when a condition of negative pressure exists in the left atrium.

2. A method of providing left side cardiac support comprising:

providing a fluid source;

introducing a fluid delivery conduit into the left atrium, the fluid delivery conduit being in communication with the fluid source, the fluid source being external of the fluid delivery conduit, the fluid delivery conduit further including an opening and a hemostatic seal sealing the opening;

introducing an intake cannula through the hemostatic seal and opening of the fluid delivery conduit and into the left ventricle, the intake cannula being coupled to a blood pump;

operating the blood pump to intake blood from the left ventricle through the intake cannula, and delivering fluid from the fluid source through the fluid delivery conduit into the left atrium when a condition of negative pressure exists in the left atrium;

wherein said fluid delivery conduit remains in communication with said fluid source during said introducing, said operating and said delivering fluid steps.

3. The method of claim 2, wherein the delivery of fluid reduces a pressure differential between a location within the left atrium and the air outside of the heart.

4. The method of claim 2, wherein the delivery of fluid eliminates a pressure differential between a location within the left atrium and the air outside of the heart.

5. The method of claim 2, wherein the intake cannula is disposed in a generally coaxial fashion within the fluid delivery conduit.

6. The method of claim 2, wherein the intake cannula is introduced into the left ventricle by insertion through the left atrium and passage through the mitral valve.

7. The method of claim 2, wherein the fluid source is a liquid source.

8. The method of claim 2, wherein the fluid source is a saline source.

9. The method of claim 2, wherein said delivering fluid from the fluid source through the fluid delivery conduit into the left atrium comprises drawing the fluid into the left atrium, wherein the condition of negative pressure existing within the left atrium comprises a pressure lower than ambient pressure and wherein the fluid source is at ambient pressure.

10. The method of claim 2, wherein a distal end of the fluid delivery conduit is positioned to terminate in the left atrium.

11. A method of providing left side cardiac support comprising:

providing a fluid source;

introducing a fluid delivery conduit into the left atrium and positioning the fluid delivery conduit so that a distal end thereof terminates in the left atrium, the fluid delivery conduit being in fluid communication with the fluid source via a supply conduit extending between the fluid delivery conduit and the fluid source, the fluid delivery conduit further including an opening and a hemostatic seal sealing the opening;

introducing an intake cannula through the hemostatic seal and opening of the fluid delivery conduit and into the left ventricle;

intaking blood from the left ventricle through the intake cannula, and delivering fluid from the fluid source through the fluid delivery conduit into the left atrium when a condition of negative pressure exists in the left atrium.

12. The method of claim 11, wherein the fluid source is connected to the fluid delivery conduit external of the intake cannula.

13. The method of claim 11, wherein the fluid source is connected to the fluid delivery conduit external of the fluid delivery conduit.

* * * * *